United States Patent [19]

Thomas

[11] 4,084,091

[45] Apr. 11, 1978

[54] CHROMATOGRAPHIC METHOD FOR DETERMINING ADDITIVE CONCENTRATION IN GASOLINE

[75] Inventor: Stephen P. Thomas, Bartlesville, Okla.

[73] Assignee: Phillips Petroleum Company, Bartlesville, Okla.

[21] Appl. No.: 695,629

[22] Filed: Jun. 14, 1976

[51] Int. Cl.$^2$ ............................................. G01N 21/38
[52] U.S. Cl. .................................. 250/302; 73/61.1 C; 250/301; 250/461 R
[58] Field of Search ............... 250/301, 302, 459, 461; 73/61.1 C

[56] References Cited

U.S. PATENT DOCUMENTS

| | | | |
|---|---|---|---|
| 3,229,505 | 1/1966 | Sanford et al. | 73/61.1 C |
| 3,614,433 | 10/1971 | Caldwell | 250/301 |
| 3,817,706 | 6/1974 | Smith | 250/302 X |
| 3,914,174 | 10/1975 | Fuchs | 73/61.1 C |

OTHER PUBLICATIONS

Effectiveness and Detection of Gasoline Additives, by Gartenmann; E., from Chemical Abstracts, vol. 75, No. 8173c.

*Primary Examiner*—Archie R. Borchelt

[57] ABSTRACT

The approximate concentration of a carburetor additive in a motor fuel is determined by a paper chromatographic method.

1 Claim, No Drawings

CHROMATOGRAPHIC METHOD FOR DETERMINING ADDITIVE CONCENTRATION IN GASOLINE

This invention relates to paper chromatrography. In one aspect, this invention relates to the determination of the concentration of a carburetor detergent in a motor fuel.

Carburetor detergents are well known in the art as necessary additives in motor fuels for the purpose of inhibiting deposits in carburetors. These deposits interfere with the normal operation of the carburetor, resulting in inefficient and/or environmentally unacceptable engine operation. It is also known in the art that the amount of such detergents in motor fuels must be maintained within certain limits. Too little of the detergent provides inadequate detergency action; too much detergent may be detrimental to the engine, such as, for example, sticking valves resulting from gummy deposits.

Laboratory methods are available for acurately determining the level of detergent dosage in a motor fuel. There is a need, however, for a reliable field test to determine the level of detergent additive in a motor fuel.

Accordingly, the object of this invention is to provide a method for determining the concentration of a detergent additive in a motor fuel.

Other objects, aspects and advantages of this invention will be readily apparent to those skilled in the art from the reading of the following disclosure.

In accordance with the present invention there is provided a rapid and reliable method for determining the approximate concentration of a detergent additive in a motor fuel comprising the steps of:

a. obtaining a sample of the motor fuel;
b. analyzing the sample by ascending paper chromatography to determine the ratio $R_f$ of the migration distance of the detergent additive relative to the migration distance of the motor fuel; and
c. correlating the ratio $R_f$ with the ratio of migration distances of at least one mixture of known concentration of the detergent additive in a motor fuel.

Carburetor detergents are generally organic compounds or mixtures of organic compounds having one or more of the following functional groups: amine, amine salt, alcohol, carboxylic acid, carboxylic acid ester, carboxamide, carboximide, sulfonic acid, sulfonic acid ester, metal sulfonate, sulfonamide, phosphate, phosphonate, and the like. Many such carburetor detergents are commercially available.

It was found that materials suitable for use as carburetor additives generally fluoresce when exposed to ultraviolet radiation. Since many of the commercial carburetor detergents are proprietary materials and are marketed as additive packages containing, in addition to the detergent, anti-icing agents, combustion promoters, carrier oils and the like, it is within the scope of this invention to include all those materials which exhibit the necessary carburetor detergency properties and which fluoresce when exposed to ultraviolet light.

The motor fuels useful in the practice of this invention are based upon any liquid petroleum fraction which is suitable for use as a motor fuel. The petroleum fraction can be obtained by any means known in the art, such as by fractionation from crude petroleum, cracking, alkylation or other refining or upgrading process.

In addition to the above-described carburetor detergents, the motor fuel can also contain other ingredients including antiknock agents such as tetraethyl lead or methylcyclopentadienylmanganese tricarbonyl; antioxidants, such as the well known hindered phenols; dyes; combustion promoters; anti-icing agents; carrier oils for the previously described "additive package"; demulsifiers; and the like. It has been observed that such conventional additives do not generally interfere with the practice of this invention.

The method of this invention is generally carried out by a procedure which involves first immersing a portion of a support, such as a paper strip or adsorbent-coated inert support, both hereinafter and in the claims referred to as the "chromatographic sorbent material," or simply as the "support," in a reservoir of the motor fuel containing the carburetor detergent and noting the initial depth of immersion. While maintaining the contact between the motor fuel and the support, the components of the fuel composition are allowed to migrate upwardly on the support by capillary action. The support should be maintained in a substantially vertical position. When the fuel composition has migrated up the support a suitable distance, the support is removed from the reservoir of motor fuel and the height of migration is noted. The volatile components of the motor fuel are allowed to evaporate under any suitable conditions, such as under ambient conditions, in a forced air draft, with gentle warming and the like. The thus-dried support is observed under a source of ultraviolet light and the height of the fluorescent band corresponding to the carburetor detergent is noted.

The approximate concentration of the carburetor detergent in the motor fuel is determined by first measuring the height of migration of the detergent and the height of migration of the motor fuel. The ratio, $R_f$, of the height of detergent migration to the height of fuel migration is indicative of the concentration of the detergent in the fuel. The concentration of the detergent in the fuel is then determined by comparing the $R_f$ value of the sample with the $R_f$ values of a series of fuel compositions containing known amounts of a given detergent. For convenience, a calibration curve for a given detergent can be prepared by plotting $R_f$ value versus concentration on an x,y coordinate system.

Several factors influence the precision and accuracy of the determinations of this invention. Smaller amounts of additives in the fuel composition generally give small $R_f$ values; i.e., the width of the additive migration zone (fluorescent band) is small compared to the width of the test solution migration. Hence the accurate measurement of the narrow additive band is difficult. The boundary of the fluorescent zone is also difficult to determine accurately because of a diffuse, rather than sharp, boundary. These factors combine to give a semi-quantitative, rather than quantitative determination.

This invention is generally intended for use in determining the presence of excessive amounts of known detergent additives in motor fuel compositions where calibration curves have ben previously prepared for comparison purposes. It is possible, however, to employ this invention to determine the presence of excessive amounts of unknown detergent additives where such calibration curves are not available by using the calibration curve for a known additive, but the accuracy of such determinations will be in question. In the case of an unknown additive, a large $R_f$ value (e.g., about 0.3 or larger) is indicative of an excessive amount of additive.

Several sources of ultraviolet radiation are commercially available which are useful in the paractice of this invention. It is convenient to use low pressure mercury vapor lamps which emit radiation primarily of 185–254 nanometers wavelength.

The chromatographic sorbent materials which are useful in the practice of this invention include paper, which is well known in the art of paper chromatography and thin-layer supports, which are well known in the art of thin-layer chromatography. Generally, strips of highly porous paper, commonly referred to as "filter paper," are useful as supports for the determination of detergent concentration in a motor fuel. The thin-layer supports consist of a thin coating, i.e., layer, of a highly porous adsorbent material, such as silica, alumina, cellulose, or the like, on an inert base, such as glass or a plastic sheet. The thickness of the adsorbent material on the inert base can be any desired and useful thickness such as from 1 micron to 1 cm. The coating can be conveniently applied as an aqueous slurry to the inert base, after which the water is evaporated leaving a uniform layer of highly porous adsorbent material.

The following example illustrates the invention:

EXAMPLE

The following runs illustrate the utility of this invention employing gasoline containing individually two commercially available carburetor detergents in varying amounts.

The carburetor detergents employed in these runs are Amoco 577-B (from Amoco) and Lubrizol 580 (from Lubrizol Corp.) both of which are proprietary materials. Amoco 577-B is nitrogen-containing and may be an amine, amide or imide derivative of a petroleum fraction. Lubrizol 580 is assumed to be an imide, such as a succinimide.

The gasoline employed with the above-described detergents in these runs is a premium pipeline base gasoline of Research Octane Number 93.0 and Motor Octane Number 85.5.

The runs were conducted as follows. A strip of paper 9.5 cm × 2.5 cm (cut from a Whatman #2 filter paper circle) was placed in a closed 120 glass vessel contaning 2 ml of the gasolne containing carburetor detergent. The paper was allowed to contact the walls of the glass vessel only at the top and bottom of the paper strip. The test solution was allowed to migrate up the paper strip until it had wetted the paper strip to a preplaced mark at a height of about 6.5 cm. The paper strip was removed fom the glass vessel and allowed to dry at atmospheric conditions. The dried paper strip was placed in a viewing cabinet containing a mercury vapor lamp which emits ultraviolet radiation of predominantly 254 nanometers wavelength. The boundary of the band of fluorescence on the irradiated paper strip was marked. The $R_f$ value (ratio of migration distance of fluorescent component to migration distance of test solution) was determined for the particular concentration of carburetor detergent employed.

Table I contains data on $R_f$ values corresponding to several different concentrations of the above described carburetor detergents.

Table I

| Conc., ptb.[a] | Amoco 577-B $R_f$ Value | Lubrizol 580 $R_f$ Value |
|---|---|---|
| 15 | 0.075 | 0.075 |
| 50 | 0.125 | 0.125 |
| 100 | 0.150 | 0.150 |
| 200 | 0.175 | 0.200 |
| 500 | b | 0.300 |
| 1000 | 0.400 | 0.475 |
| 2000 | 0.600 | b |

[a] Concentration of additive in pounds of additive per thousand barrels of fuel.
[b] Not determined.

The data in Table I show that the $R_f$ values corresponding to the carburetor detergents employed increased as the concentration of detergent increased, thus providng a calibration curve of $R_f$ value versus concentration for a method of determining the amount of detergent present in the fuel.

Reasonable variations and modifications, which will be apparent to those skilled in the art, can be made in this invention without departing from the spirit and scope thereof.

What is claimed is:

1. A method for determining the approximate concentration of a detergent additive in gasoline which comprises the steps of:
   a. obtaining a sample of said gasoline;
   b. analyzing said sample by ascending paper chromatography to determine the ratio $R_f$ of the migration distance of said additive relative to migration distance of said gasoline, by contacting a portion of a chromatographic sorbent material with said gasoline containing said additive for a period of time sufficient to allow said gasoline and said additive to migrate upwardly on said sorbent material, removing said sorbent material from contact with said gaoline, noting the initial height of contact of said gasoline with said sorbent material, noting the height of migration of said gasoline on said sorbent material, allowing said gasoline to evaporate from said sorbent material, irradiating said sorbent material with an ultraviolet light source whereby said additive fluoresces, noting the height of the fluoresence corresponding to said additive, and thereafter determining said ratio $R_f$; and
   c. correlating said ratio with the ratio of migration distances of at least one mixture of known concentration of said additive in said gasoline.

* * * * *